US006793670B2

(12) United States Patent
Osorio et al.

(10) Patent No.: US 6,793,670 B2
(45) Date of Patent: Sep. 21, 2004

(54) MULTI-MODAL SYSTEM FOR DETECTION AND CONTROL OF CHANGES IN BRAIN STATE

(76) Inventors: Ivan Osorio, 4005 W. 124th St., Leawood, KS (US) 66209; Naresh C. Bhavaraju, 6909 W. 51st Pl., Apt. 3B, Mission, KS (US) 66202

( * ) Notice: Subject to any disclaimer, the term of this patent is extended or adjusted under 35 U.S.C. 154(b) by 0 days.

(21) Appl. No.: 10/683,647

(22) Filed: Oct. 10, 2003

(65) Prior Publication Data

US 2004/0082984 A1 Apr. 29, 2004

Related U.S. Application Data

(60) Provisional application No. 60/418,154, filed on Oct. 11, 2002.

(51) Int. Cl.$^7$ ................................................ A61F 7/12
(52) U.S. Cl. ......................................... 607/113; 607/99
(58) Field of Search ............................ 607/96, 99, 113

(56) References Cited

U.S. PATENT DOCUMENTS

| | | | | |
|---|---|---|---|---|
| 3,298,371 A | * | 1/1967 | Lee .............................. | 606/23 |
| 5,995,868 A | * | 11/1999 | Dorfmeister et al. ....... | 600/544 |
| 6,128,527 A | * | 10/2000 | Howard et al. ............. | 600/544 |
| 6,190,378 B1 | | 2/2001 | Jarvinen | |
| 6,248,126 B1 | | 6/2001 | Lesser et al. | |
| 6,549,804 B1 | | 4/2003 | Osorio et al. | |
| 6,660,026 B2 | * | 12/2003 | Larnard et al. ............. | 607/104 |

OTHER PUBLICATIONS

Topographic and Toposcopic Study of Origin and Spread of the Regular Synchronized Arousal Pattern in the Rabbit, by H. Petsche and Ch. Stumpf, *Electroenceph. Clin. Neurophysiol.*, 12:589–600 (1960).

Étude sur Modèle des Méthodes de Détection EEG, by L. Jami, A. Fourment. J. Calvet et M. Thiefry, *Electroenceph. Clin. Neurophysiol.*, 24:130–145 (1968).

The Significance of the Cortex for the Travelling Phenomena of Brain Waves, by H. Petsche and J. Šterc, *Electroenceph. Clin. Neurophysiol.*, 25:11–22 (1968).

Influence of Cortical Incisions on Synchronization Pattern and Travelling Waves, by H. Petsche and P. Rappelsberger, *Electroenceph. Clin. Neurophysiol.*, 28:592–600 (1970).

Properties of Cortical Seizure Potential Fields, by H. Petsche, P. Rappelsberger and R. Tappl, *Electroenceph. Clin. Neurophysiol.*, 29:567–578 (1970).

Cerebral Cortex: Cytoarchitecture and Electrophysiology, by Elliott M. Marcus, In: "An Introduction to the Neurosciences," by B. A. Curtis, S, Jacobson and E. M. Marcus, Ch. 20, pp. 447–482, W. B. Saunders, Philadelphia (1972).

Exacerbation of Seizures in Children by Carbamazepine, by O. Carter Snead, III, and Lynn C. Hosey, *The New England Journal of Medicine*, 313(15):916–921 (1985).

(List continued on next page.)

*Primary Examiner*—Roy D. Gibson
(74) *Attorney, Agent, or Firm*—Donald R. Schoonover

(57) ABSTRACT

A multi-purpose electrode mechanism for detection and control of changes in brain state includes a shaft portion and extendible elements structured for insertion into target tissue of the brain of a subject patient, cooling means configured to operatively apply cooling therapy to the target tissue, stimulation means having at least one electrical contact structured to operatively apply electrical stimulation therapy to the target tissue, sensing means including at least one sensor monitoring a biological signal of the subject patient, control means responsive to the sensing means wherein the control means is structured to, in response to signals from the sensing means that indicate the presence of a predetermined physiological condition or occurrence of an undesirable state change, automatically cause the cooling means and/or the stimulation means to initiate or terminate the cooling therapy and/or the electrical stimulation therapy respectively and an energy source for powering the various components of the multi-purpose electrode mechanism.

21 Claims, 5 Drawing Sheets

OTHER PUBLICATIONS

Antiepileptic Drug Intoxication: Factors and Their Significance, by Ramon Manom–Espaillat, Thomas H. Bernstine, Bernd Remler, Ronald C. Reed and Ivan Osorio, *Epilepsia*, 32(1):96–100 (1991).

Kindling–Induced Potentiation inthe Piriform Cortex, by R. J. Racine, K. A. Moore and C. Evans, *Brain Research*, 556:218–225 (1995).

Stimulus–Dependent, Reciprocal Up– and Downregulation of Glutamic Acid Decarboxylase and $Ca^{2+}$/Calmodulin–Dependent Protein Kinase II Gene Expression in Rat Cerebral Cortex, by F. Liang, P.J. Isackson and E. G. Jones, *Exp. Brain Research*, 110:163–174 (1996).

Do Antiepileptic Drugs as a Cause of Worsening Seizures, by E. Perucca, L. Gram, G. Avenzini and O. Dilac, *Epilepsia*, 39(1):5–17 (1998).

Effects of Applied Currents on Spontaneous Epileptiform Activity Induced by Low–Calcium in the Rat Hippocampus, by R. James Warren and Dominique M. Durand, *Brain Research*, 806:186–195 (1998).

Refractory Idiopathic Absence Status Epilepticus: a Probable Paradoxical Effect of Phenytoin and Carbamazepine, by Ivan Osorio, R. C. Reed adn Jill N. Peltzer, *Epilepsia*, 41(7):887–894 (2000).

Mechanisms of Deep Brain Stimulation: Excitation or Inhibition, by Jerrold L. Vitek, *Movement Disorders*, 17(3), S69–S72 (2002).

Mechanisms of Deep Brain Stimulation, by Alim L. Benabid, Abdelhamid Benazzous and Pierre Pollak, *Movement Disorders*, 17(3), S73–S74 (2002).

\* cited by examiner

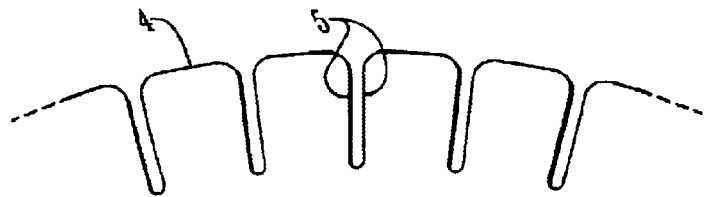
FIG.1
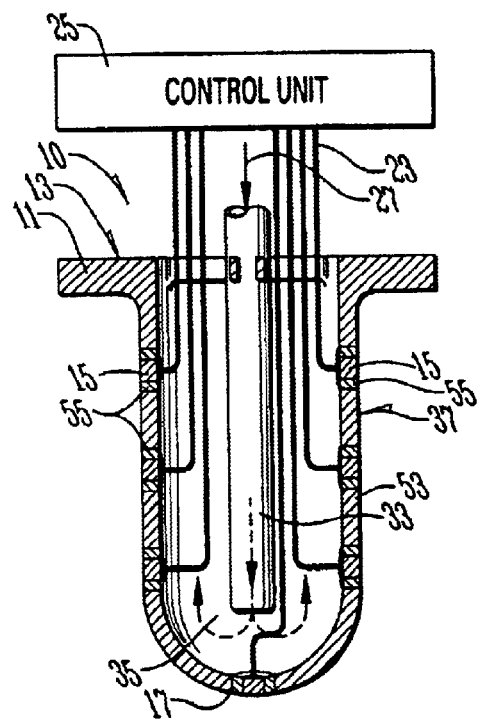
FIG.2a
FIG.2b

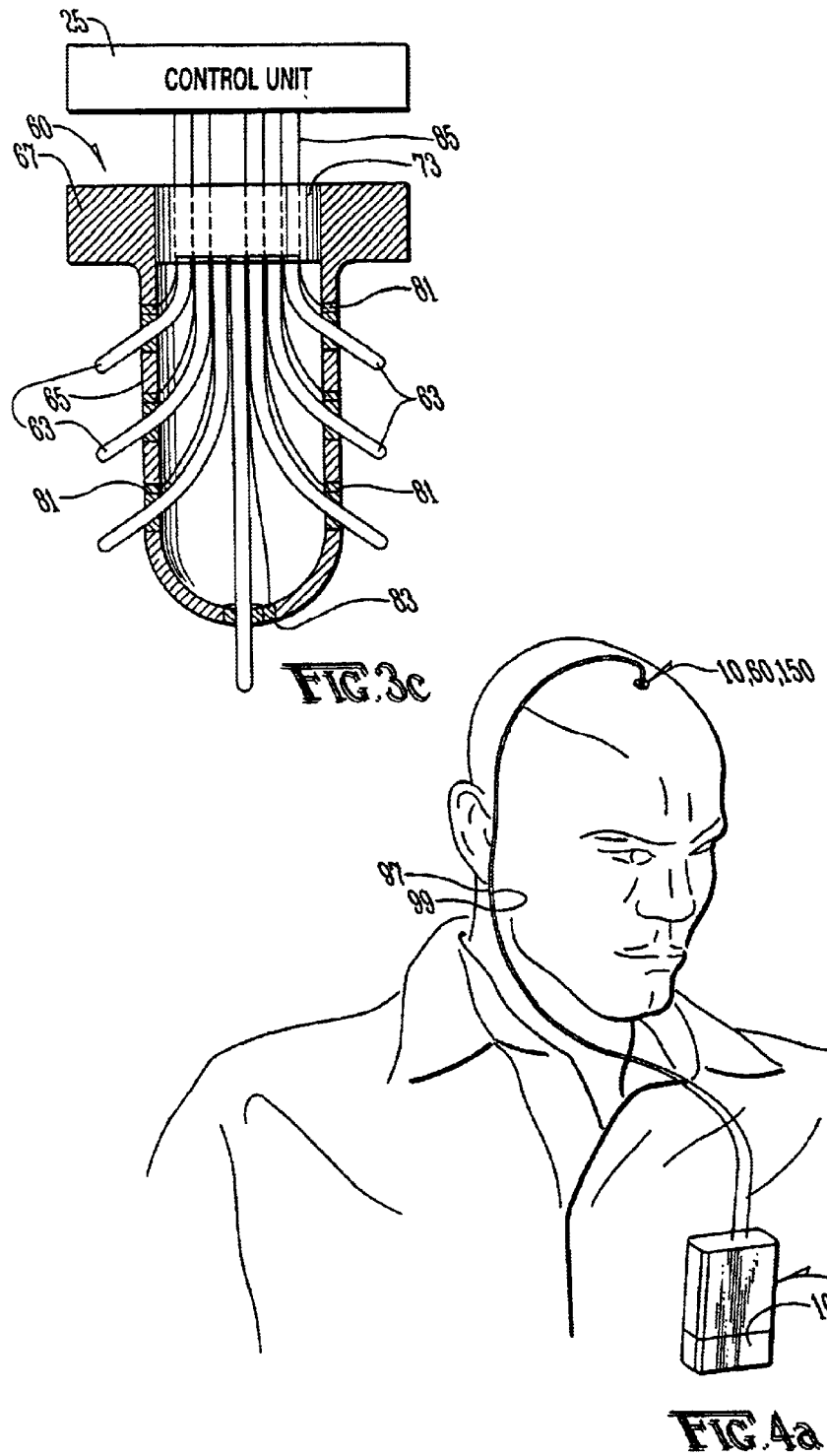

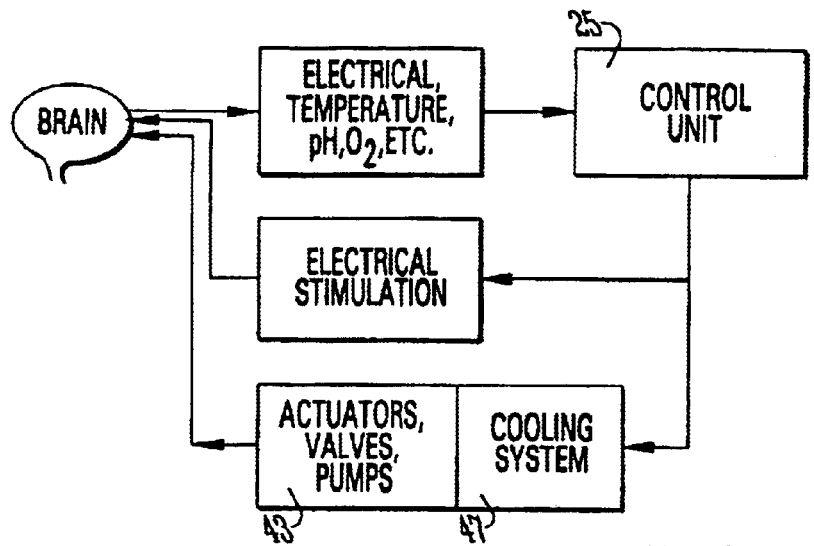
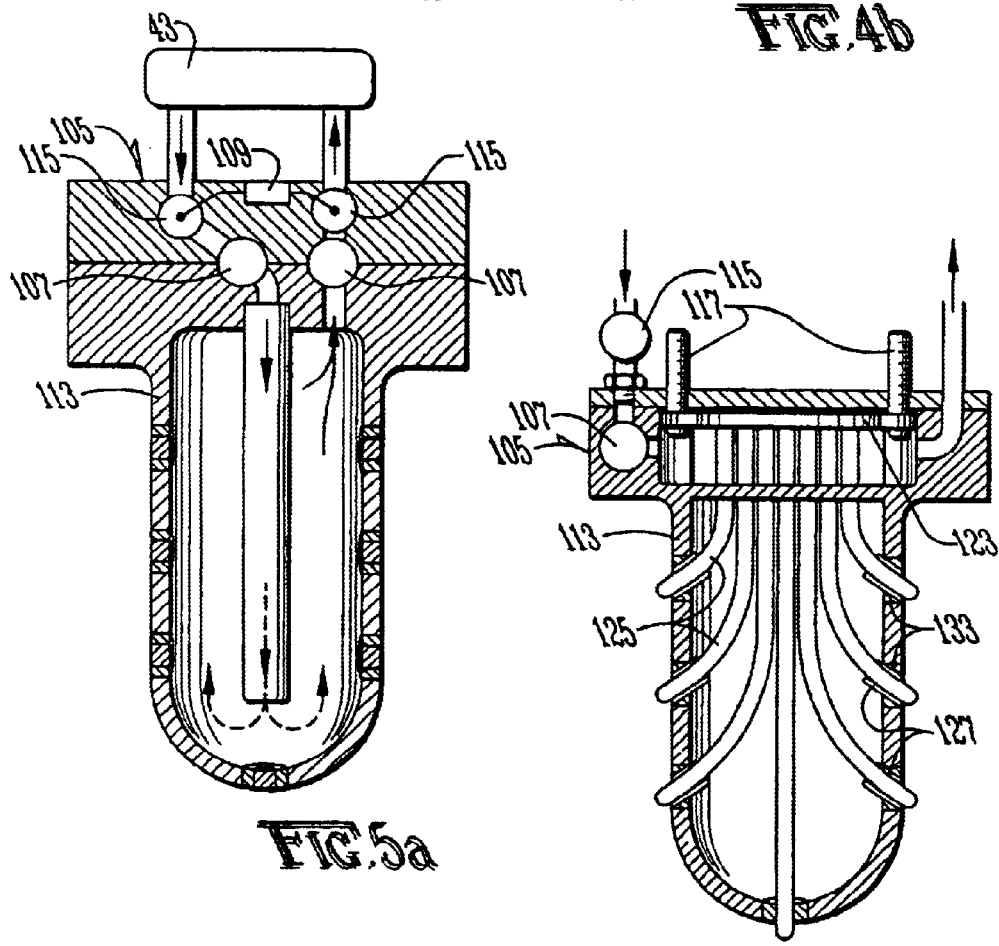

MULTI-MODAL SYSTEM FOR DETECTION AND CONTROL OF CHANGES IN BRAIN STATE

CROSS REFERENCE TO RELATED APPLICATIONS

This application is based on Provisional Patent Application Ser. No. 60/418,154 of Ivan Osorio et al, filed Oct. 11, 2002.

BACKGROUND OF THE INVENTION

1. Field of the Invention

The present invention is related to medical treatments involving the human brain and, more specifically without limitation, to real-time automated prediction/detection and non-pharmacological contingent, or closed-loop prevention/control or blockage of brain state changes using electrical or thermal signals either individually or simultaneously for detection or prediction of seizures or other changes in brain states; automated timely and safe delivery of cryogenic therapies; quantitative assessment of their efficacy and safety; and means for optimization thereof.

2. Discussion of the Related Art

Neuronal and, by extension, brain metabolic and electrical activity of poikilothermic and homeothermic animals are without exception temperature-dependent. Low temperatures (below 35° C.) in homeotherms, and more specifically in humans, have an easily discernible effect on behavior and on an EEG, which is a reliable index of cortical electrical activity. At such temperatures, cerebral blood flow, oxygen and glucose consumption become depressed and, due to tight electro-metabolic coupling, so does neuronal function and its by-product, electrical activity. Brain cooling has a protective effect on the integrity of its tissue, a feature that has therapeutic applications.

For example, hypothermia minimizes damage in models of brain ischemia by decreasing both the metabolic demand of the brain tissue and the production of glutamate and dopamine, which under certain conditions can be excitotoxic. These effects make hypothermia well-suited for the treatment of neurological diseases that are characterized by the following:

1) absolute or relative, global or local neuronal hyper excitability, such as in epilepsy;
2) an imbalance in the degree of neuronal activity between/among structures which form part of a functional network, such as in Parkinson's disease;
3) reduction in the supply of energy substrates, such as in stroke; and
4) activation/release of pathoclitic enzymes, such as in trauma, stroke, infection or prolonged/frequent seizures (status epilepticus).

Cooling can also be used for functional cortical localization or assessment of cognitive functions to assist in neurosurgical planning. Cryogenics has definite important advantages over electrical stimulation, the current standard for cortical localization, as follows:

a) cooling, unlike electrical stimulation (ES), does not precipitate seizures; and
b) unlike ES, which requires at least two stimulating electrodes and which has the potential to reach all structures between the electrodes and even those remote to them via existing neural pathways, the effects of cooling remain more localized and are more gradual than ES, thus providing more selective and interpretable information and also a higher therapeutic index.

Although cooling of brain tissue has been an object of several prior art approaches for various medical treatments, most of those approaches have been limited to cooling the most superficial layers of small cortical areas or in some cases just the scalp. Some other prior art approaches utilize cryogenic energy to ablate or destroy brain tissue. Cooling for the sole purpose of tissue ablation/destruction requires processing of very few, if any, input signals and parameter controls whereas reversible safe cooling of brain tissue for control of state changes such as seizure blockage, as taught by the present disclosure for seizure blockage purposes, is a highly time-sensitive task. For example, while methods for measuring tissue properties, such as thermal conductivity for the purpose of controlling the extent and degree of freezing, which is an irreversible destructive procedure, are disclosed in U.S. Pat. No. 6,190,378, that procedure is neither time-sensitive nor dependent on the detection of changes in electrical or thermal signals as required for seizure blockage using reversible cooling. No prior art reference appears to disclose seizure blockage as taught herein; references that border on such an application appear to have very limited usefulness or relevance for the medical applications disclosed herein. One prior art reference discloses means to block seizures through reversible cooling, namely U.S. Pat. No. 6,248,126 to Lesser et al, but has significant limitations, which make it highly unlikely that seizures can be blocked using such a device, even if the seizures originate from exposed gyri, designated by numeral 4 in FIG. 1, for the following reasons:

1) placement of the device of the '126 patent over the most superficial cortical layer of exposed gyri as taught by the '126 patent prevents timely cooling of deeper cortical layers (IV–VI) from where most seizures originate because (a) there are no means for attachment and, as a result, the cooling device floats over the cerebrospinal fluid and the fluid currents, through convection, carry cooling energy away from the target site thereby slowing down the rate at which tissue cooling can occur at the most superficial cortical layers; and (b) thermal diffusivity of brain tissue is such that rapid or timely cooling of deeper layers to block seizures can not take place; and 2) the majority of cortical gyri are not exposed, designated by numeral 5 in FIG. 1, and thus are not amenable to cooling using such a device.

Epilepsy affects about 2.7 million people in the United States and about 60 million worldwide. Approximately 30% of this population has pharmaco-resistant epilepsy, defined as at least one monthly seizure despite treatment with appropriate drugs at therapeutic concentrations. New therapies, which are both safe and effective, are required, given the existent, unmet need. Cooling of brain tissue is one such therapy with great potential as its effects are fully reversible and safe since the range of effective temperatures has no adverse effects on tissue viability or integrity and it is not known to precipitate or worsen seizures. While as early as 1974, it was shown that lowering the temperature of the midbrain prevents epileptiform activity, this therapeutic modality has received little attention due mainly to lack of suitable implantable devices and of interest in therapies other than pharmacological ones. Newly published evidence lends more support for an anti-seizure role for cooling of brain tissue. For example, U.S. Pat. No. 6,248,126 to Lesser et al discloses the use of a device based on the Peltier effect for cooling small areas of the cortical surface for seizure control. That device has important practical limitations, as described below, which translate into reduced efficacy and applicability. For example, that device does not provide a means to transfer heat (or cooling) in a timely manner from the surface to deeper neocortical regions from where seizures originate, which considerably limits efficacy since the delay in delivering therapy to critical regions allows the seizure to spread and gain intensity. This delay is explained by the fact that temperature gradients are steep and limit cooling to the immediate vicinity of the electrode, which necessitates that the cooling source be located as close to the target as possible for the therapy to be effective. Thermal diffusivity brain models reveal that lowering the temperature of a region located 5 mm from the cooling source, which is the average width of the cortex, from 37° C. to 16° C. takes approximately thirty seconds. Since placement of a Peltier device as taught by Lesser et al is on the cortical surface and the distance between that Peltier device and the seizure-generating cortical layers is about 5 mm, it is highly unlikely that they can be cooled down sufficiently timely to block seizures and prevent their spread. For any contingent therapy to be efficacious, it must reach the site of origin within five seconds of seizure onset. The ability to rapidly reach the seizure-generating tissue (epileptogenic region) is essential for the success of cryogenic therapy. Moreover, the device and approach of the '126 patent do not have the means to monitor tissue electrical activity required to maximize efficacy, minimize the risk of freezing the tissue, assess therapeutic efficacy, and operate efficiently. Other prior art cooling catheters and probes are not suitable for use in epilepsy.

Cooling offers certain advantages over electrical stimulation for control of state changes or of cortical or subcortical functions as follows:

a) the only critical control parameter in cooling therapy is temperature as compared to intensity, frequency, pulse width, waveform, size and orientation of the field orientation, which determine efficacy and safety of electrical stimulation;

b) cooling has a greater safety margin than electrical stimulation because of the less instantaneous nature of the change in temperature particularly at the electrode-tissue interface, as opposed to charge deposition over the area covered by the electrical field and the known ability of electrical stimulation to induce seizures when certain parameters are utilized; and c) cooling allows good-quality recording of electrical brain signals during cryogenic therapy for continuous real-time assessment of efficacy, an important function which can not be accomplished during delivery of electrical therapy, since electrical therapy saturates amplifiers and distorts brain electrical activity, not only for the duration of the electrical stimulation but also for a few seconds after its conclusion, which precludes meaningful analysis and valid interpretation of brain electrical signals. However, since electrical diffusivity is much higher than thermal diffusivity, electrical therapy may have quicker effects than is realizable from cryogenic therapy.

What is needed is a multi-purpose electrode, which the present invention provides for single, dual, simultaneous or sequential electrical and/or cryogenic therapy for control of brain state changes or of cortical and subcortical functions. What is also needed is a cooling device that is principally, but not only, activated in response to a cue including, but not limited to, detection or prediction of a seizure, to thereby minimize power consumption, a prerequisite for miniaturization and implantation.

SUMMARY OF THE INVENTION

The improvement of the multi-purpose electrode mechanism of the present invention for prediction or detection and control of changes in brain state includes a shaft portion structured for insertion into target tissue of the brain of a subject patient, cooling means configured to operatively apply cooling therapy to the target tissue, sensing means including at least one sensor monitoring a biological signal of the subject patient, control means responsive to the sensing means wherein the control means is structured to, in response to signals from the sensing means that indicate the occurrence of a change of state, automatically cause the cooling means to initiate or terminate the cooling therapy, and an energy source for powering the various components of the multi-purpose electrode mechanism.

The cooling means of the multi-purpose electrode mechanism includes at least one extendable element housed within the shaft portion and structured to be extended outwardly from the shaft portion into target tissue, either manually or by motor means. The at least one extendable element includes at least one cooling element, which may be hollow with a closed distal end and a dividing wall that extends from near the proximal end to near the distal end thereof that separates the at least one cooling element into side-by-side first and second channels with fluid flow communication between the first and second channels at the distal end thereof, or may be constructed of a solid material having high thermal conductivity. The cooling means also includes either a reservoir for containing coolant and pumping means structured to pump coolant to and from the reservoir and to the at least one cooling element, or a refrigerant source containing refrigerant at an elevated pressure, distribution means for distributing the refrigerant from the refrigerant source to the at least one cooling element, and means for removing the refrigerant from the cooling element or from the shaft portion.

The sensing means may include a sensor or sensors positioned in one or more of the extendable elements and may include one or more sensor mounted on the shaft portion to operatively contact target tissue adjacent thereto.

The multi-purpose electrode mechanism may also include stimulation means having at least one electrical contact structured to operatively apply electrical stimulation therapy to the target tissue wherein the control means, in response to signals from the sensing means that indicate the occurrence or presence of a change of state, is structured to automatically cause the stimulation means to initiate or terminate the electrical stimulation therapy.

The cooling means of multi-purpose electrode mechanism may include at least one thermoelectric device.

The sensing means and control means of the multi-purpose electrode mechanism may be structured to sense and control one-, two-, and/or three-dimensional configurations. The sensing means may be structured to sense chemical signals arising from ions, neurotransmitters and/or pH, and/or to sense physical signals arising from infrared, pressure and/or acoustics.

PRINCIPAL OBJECTS AND ADVANTAGES OF THE INVENTION

The principal objects and advantages of the present invention include: providing a multi-purpose electrode that can be used to detect relevant one-, two-, or three-dimensional changes in electrical or thermal or other types of signals reflective of brain state; providing such a multi-purpose electrode that can be used to control or prevent changes in brain state by, for example, lowering, in real-time, brain temperature at the cortex, white matter, or subcortical structures for one-, two-, or three-dimensional detection or treatment purposes; providing such a multi-purpose electrode that can be used to evaluate the efficacy of therapy in real time while the therapy is being delivered and optimize it; providing such a multi-purpose electrode that can provide electrical, thermal, or other feedback to a control system connected to the electrode; providing such a multi-purpose electrode that can be used to evaluate the safety of therapy in real time while the therapy is being delivered to thereby minimize the risk of injury to tissue being treated; providing such a multi-purpose electrode that can be used to detect and control in a timely fashion pathological changes in brain, spinal cord, spinal roots, or peripheral nerves of states such as stroke, trauma, depression, pain movement disorders, cognitive functions, behavior or emotions or physiological ones, such as changes in level of attention, drowsiness, and others; providing such a multi-purpose electrode that may be used to effect cooling of brain tissue in response to changes in signals other than electrical or thermal, which may occur prior to or at the onset of changes in brain state, such as signals arising from cardiovascular, autonomic, chemical (pH, $[Ca^{++}]$, $[K^+]$, amino acids, energy substrates, catabolic products, free radicals, etc.) or physical (pressure, sound, optical, etc.) phenomena; and generally providing such a multi-purpose electrode that is reliable in performance, capable of long lasting life, and particularly well-adapted for the proposed usages thereof.

Other objects and advantages of this invention will become apparent from the following description taken in conjunction with the accompanying drawings wherein are set forth, by way of illustration and example, certain embodiments of this invention.

BRIEF DESCRIPTION OF THE DRAWING FIGURES

FIG. 1 is a depiction of the cortex, showing both exposed and unexposed portions.

FIG. 2a depicts a multi-purpose electrode for detection and control of changes in brain state, according to the present invention.

FIG. 2b is a schematic representation of the multi-purpose electrode for detection and control, through cooling, of changes in brain state depicted in FIG. 2a.

FIG. 3c is yet another depiction of the modified embodiment of the multi-purpose electrode for detection and control of changes in brain state similar to FIG. 3b but also showing a sensor thereof.

FIG. 4a is a schematic representation of the multi-purpose electrode for detection and control of changes in brain state connected to a subject patient.

FIG. 4b is a schematic representation of various components of the multi-purpose electrode for detection and control of changes in brain state connected to the brain of a subject patent.

FIGS. 5a and 5b depict various components of the multi-purpose electrode for detection and control of changes in brain state for effecting the flow of coolant or refrigerant therethrough.

DETAILED DESCRIPTION OF THE PREFERRED EMBODIMENTS

Figure 3A:
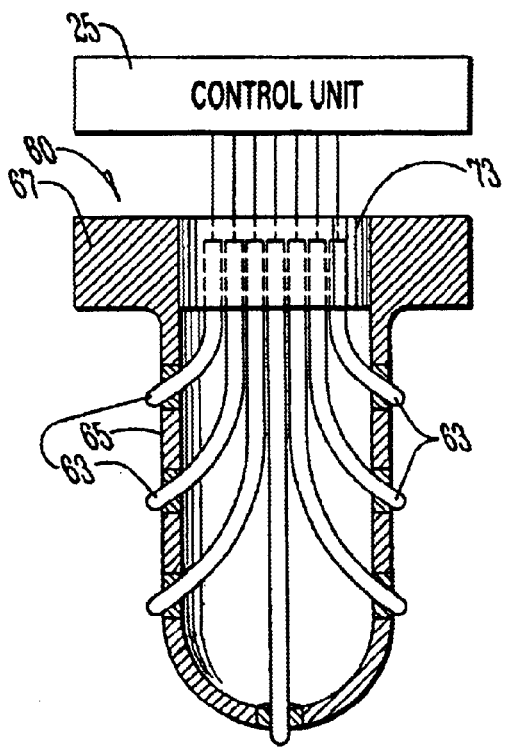
FIG. 3a is a depiction of a modified embodiment of the multi-purpose electrode for detection and control of changes in brain state having extendable elements housed in a shaft portion wherein the elements are shown in a retracted configuration.

As required, embodiments of the present invention are disclosed herein, however, it is to be understood that the disclosed embodiments are merely exemplary of the invention, which may be embodied in various forms. Therefore, specific structural and functional details disclosed herein are not to be interpreted as limiting, but merely as a basis for claims and as a representative basis for teaching one skilled in the art to variously employ the present invention in virtually any appropriately detailed structure.

The present invention disclosed herein overcomes the limitations of prior art approaches for utilizing cooling effects for detection and control of changes in brain state by: a) monitoring and processing brain electrical and/or thermal signals in real-time for the prediction and detection of seizures or of undesirable brain state changes; b) utilizing feedback controls and means for timely delivery, and cessation of delivery, of cooling to epileptogenic tissue to optimize device performance, and for therapeutic efficacy and safety in an individualized manner. The present invention substantially improves state-of the-art approaches by providing:

1) automated means for cooling brain tissue in a temporally selective manner, i.e., in response to seizure detections or to neuronal behavior or conditions associated with a high probability of seizure occurrence or of other changes in brain states, using the brain's electrical activity or temperature input signals;

2) means for cooling brain tissue in a spatially selective manner to thereby decrease undesirable side effects and power consumption by the device and to increase therapeutic efficiency by limiting delivery of cooling therapy to only a target site of interest;

3) automated feedback to and from a cooling device for regulating and keeping the temperature of cooling being applied to target tissue within a safe and therapeutic range for the subject patient based on measurements of tissue temperature or electrical activity changes of the brain; and 4) means for rapid delivery of cooling to epileptogenic tissue or to tissue that mediates changes in brain state.

The invention disclosed herein is based on the knowledge that (i) seizures or other changes in brain states are manifested with characteristic changes in electrical activity, and (ii) seizures and other changes in brain states are accompanied by changes in local tissue temperature.

Based on the disclosure herein, it will be evident to those familiar with the pertinent art, that the disclosed invention significantly enhances the ease of use, safety and efficacy, of cryogenic therapy over the approaches of the prior art.

The present invention utilizes, in its preferred embodiments, a unitized electrode which simultaneously allows (i) detection of changes in brain state using electrical, thermal, chemical, physical, or other types of signals, and (ii) delivery of cryogenic therapy, and simultaneously of electrical stimulation therapy if desired, to all cortical layers including at the top, bottom, and inner wall of exposed and unexposed gyri, and to the white matter and subcortical structures if desired, thereby overcoming the inherent limitations imposed by low thermal diffusivity in brain tissue and minimizing the thermal exchange losses through convection that limit applicability of prior art approaches. Those skilled in the pertinent art will realize from the disclosure herein that other means of delivering cooling to, or exchanging thermal energy with, brain tissue may be used for detection and control of state changes.

The present invention includes several embodiments that reflect different modes of operation for different applications. Nervous system or brain state changes may be predicted or detected using sensors for changes in temperature, electrical activity, chemical or physical signals that activate delivery of cooling therapy or of electrical stimulation therapy, or both, by the multi-purpose electrode of the present invention to the target site or sites of interest. As relevant signals at those sites reach a critical level indicative of state change, the target tissue or region receives cooling therapy in a controlled manner until the detected abnormality is eliminated, or a safety constraint such as a temperature of 4° C. at the electrode-tissue interface is reached.

In a modified embodiment of the present invention, brain tissue which mediates or generates state changes is precooled and continuously maintained in-between state-changes at a temperature that is lower than normal but is above that which blocks the state transition, to thereby minimizes both power dissipation and delay in applying therapy. Upon detection of signal changes indicative of an impending change of state, the electrode of the present invention is activated so that the tissue or region temperature may be further cooled to a desired therapeutic level. This approach, which speeds up the effects of cooling, may be used in cases wherein the rate of temperature change as a function of tissue volume or area of a target tissue or region is not adequate for control purposes as determined by real-time thermal or electrical feedback, an aspect not provided by prior art approaches. In another modified embodiment of the present invention, electrical stimulation therapy is applied in addition to cooling or cryogenic therapy, wherein the electrical stimulation therapy is delivered simultaneously with, before, or after cryogenic therapy.

FIG. 1 depicts the human cortex. The electrical activity generated in the deeper layers is either not accessible or accessible only to electrodes placed over the most superficial layer of exposed gyri, only after a delay from the time the electrical activity is actually generated. This results in either no detection for unexposed gyri or late detection of state changes, limitations not recognized or taken into account by present state-of-the-art approaches which are greatly compounded by an even larger delay, when attempting to apply cooling therapy to deeper layers when the cooling source is placed over the cortical surface as taught by the prior art.

Basic design criteria of the electrodes of the present invention are disclosed in U.S. patent application Ser. No. 10/622,238 to Ivan Osorio et al, filed Jul. 18, 2003, which is incorporated herein by reference. Briefly, the electrodes of the present invention enable simultaneous measurement of brain signals (thermal, electrical, chemical or physical signals) from exposed and unexposed cortical gyri, both from their depths and from their surfaces, thereby providing precise localization and delivery of therapy or other means of control to any of those locations without appreciable delay and with precision otherwise not previously attainable. By simply increasing the length of the electrodes of the present invention, the recording or sensing and control range of the electrodes may be considerably increased. In other words, signals may be recorded simultaneously, without delay and with great precision, from the surface and depths of the cortex, from the white matter, and from radially aligned subcortical structures such as the thalamus, using the same electrode.

FIG. 2a depicts an embodiment of the present invention 10 that comprises electrode structure 13 with at least one sensor 15 for acquiring physical (i.e., electrical, thermal), chemical (i.e., ion concentration, oxygen, neurotransmitters) or other types of biological signals, and at least one cooling surface 17. Temperature sensing and monitoring may be achieved with small thermocouples, thermistors, surface acoustic wave technology or other suitable miniature or micro temperature sensors. For other monitoring or recording signals, such as those arising from pH, $O_2$ saturation, neurotransmitters, etc., various miniature or micro sensors are presently available for such purposes. When configured to record electrical activity, sensor 15 may also be used for injecting current into, or for applying electrical stimulation therapy to, brain tissue. Contacts or sensors 15 used for recording or monitoring purposes are connected to conductors 23 that carry signals to and from the sensors 15 to control apparatus 25 situated outside the electrode 13. Fluid 27, such as saline cooled to an appropriate temperature, flows through an inner tube 33 to an outer cavity 35 defined by shaft 37 and back into a coolant reservoir 43, as schematically depicted in FIG. 2b. Although various coolants may be used, sterile saline with preservatives or antimicrobials is preferred due to its biological safety and high thermal capacity.

The circulation of coolant 27 through the tube 33 and cavity 35 is controlled by units, depicted in FIGS. 4 and 5 and as hereinafter described, which operate based on inputs from sensors 15. Control units 25, see FIGS. 4a and 4b, may include a microprocessor in addition to analog or digital apparatus and are connected to a coolant circulating system 43 that may include devices 47, such as actuators, valves and/or pumps, to control the flow of coolant or refrigerant through the electrode 10. Prediction and detection of state change using any of the signals described herein, and as disclosed in U.S. Pat. No. 6,549,804 to Ivan Osorio et al, issued Apr. 15, 2003 which is incorporated herein by reference, enables circulation of coolant 27 through the electrode 10, which circulation can be terminated based on a pre-determined threshold of sensor signals for efficacy or safety. The shaft 37 also includes insulating portions 53 for separating cooling surfaces 17, sensors and electrical contacts 15 from each other. The insulating portions 53 are constructed of materials such as polyurethane, Teflon or other suitable materials, such as Tecoflex™ or Silastic™ for example, that preserve the flexibility of the shaft 37. Those skilled in the art can appreciate that the location and extent of the insulating portions 53 and of the cooling surfaces 17 can be varied according to any particular application or the shape of the electrode. Coolants 27 or refrigerants are prevented from leaking into the surrounding brain tissue by using medical, biocompatible seals 55, such as those presently available for such purposes. The mechanisms for transferring coolant or for cooling may include micro-fluidic pumps, miniature heat pumps, miniature heat absorption systems, thermoelectric coolers, miniature evaporation systems working with cryogenic fluids or other presently available pumps, which can facilitate fluid flow through microchannels, such as the tubes inside the electrodes described herein. Those skilled in the art can appreciate that signal transmission between sensors 15 and control unit 25 may be wireless. In that event, the electrode 10 would include a miniaturized transmitter mounted in the base 11.

Figure 3B:
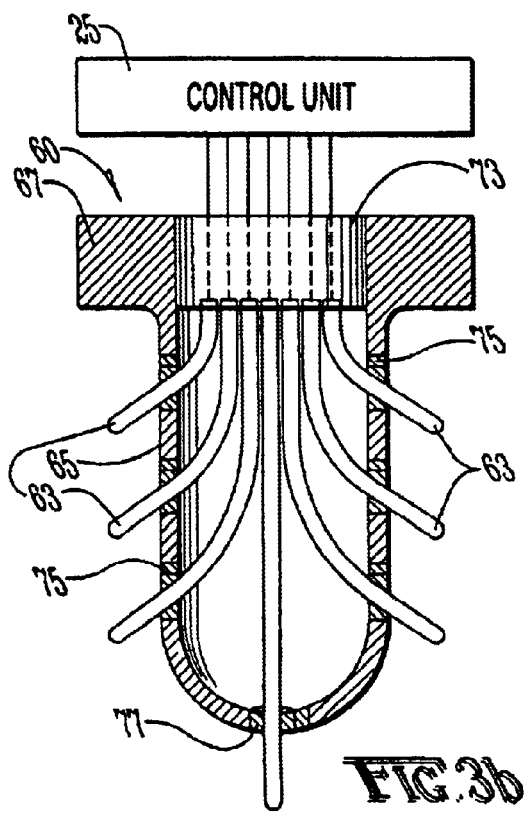
FIG. 3b is another depiction of a modified embodiment of the multi-purpose electrode for detection and control of changes in brain state similar to FIG. 3a but showing the retractable elements in an extended configuration.

FIGS. 3a–3b depict a modified embodiment 60 of the present invention wherein extendable elements 63 can be extended into the surrounding tissue after a shaft portion 65 of the electrode 60 is implanted into a desired target region or tissue. The electrode structure 60 of this embodiment includes a base portion 67. The shaft portion 65 is first inserted into the target tissue after which the extendable elements 63 can be extended into the surrounding tissue to thereby increase the contact area between the extendable elements 63 and the tissue, wherein the extendable elements 63 are extended either manually or by using tiny motors or other mechanical or electromechanical means. Each of the extendable elements 63 used for cooling therapy, sometimes referred to herein as a cooling element 63, is hollow and made of biocompatible materials with high thermal conductivity such as gold, platinum, or other suitable thermally conductive material and may include a dividing wall, see inset of FIG. 3a, that allows coolant to be circulated from a proximal end thereof to a distal end thereof along one side of the extendable element 63 and to be circulated from the distal end thereof to the proximal end thereof along the other side of the extendable element 63. The extendable elements 63 used for cooling therapy are automatically filled with coolant in response to prediction or detection of brain state changes as signaled by sensors to control apparatus. Upper ends of the extendable elements 63 used for cooling therapy have valves 47 controlled by control apparatus for controlling the flow of coolant or refrigerant through the electrode 60. Coolant is pumped into the cooling elements 63 by a micro-pump located at an upper end 67. The ratio of the diameter of the protruding tubes to the diameter of the shaft may be larger than that depicted in FIG. 3, to allow implantation of more probes/unit volume, to thereby increase the rate of cooling without causing more tissue damage. This probe may be used to sense and control in one-, two-, or three-dimensions, depending on the orientation of the protruding tubes in reference to the shaft.

The present invention enables successful control of brain state changes, such as prevention or blockage, or successful observance of safety constraints in response to sensor signals provided to the control apparatus that causes the control apparatus to automatically initiate and automatically terminate coolant flow through cooling elements 63 and to also pump any residual coolant from the shaft portion 65 back into reservoir 43. In an application of the present invention, see FIG. 3b, electrical, temperature and other sensors 75 are located in the shaft portion 65 of the electrode 60. The shaft portion 65 includes insulating portions 77 for separating cooling surfaces 63 from electrical contacts 75, and sensors 75 from each other. As before, the insulating portions 77 are constructed of materials such as polyurethane, Teflon or other suitable materials, such as Tecoflex™ or Silastic™, that preserve flexibility of the shaft portion 65. Those skilled in the art can appreciate that location and extent of the insulating portions 77 and cooling surfaces 63 can be varied as required by an application thereof.

In some applications of the present invention, selected ones of the extendable elements 63 may also act as electrical sensors, see FIG. 3c. Other sensors 83 for temperature, chemical, and other signals may also be disposed in the shaft portion 65, although such sensors may also be positioned within the extendable elements 63. Coolant or refrigerant is prevented from leaking into the surrounding tissue by using medical, biocompatible seals 81, such as seals presently available for such purposes. The cooling or sensor elements 63 protruding from the shaft portion 65 enable three-dimensional recording and control/therapy of brain state-changes, which provides greater range/scope, precision and flexibility for improved efficacy and safety, features not provided by prior art devices. All sensors 75, 83 are connected in communication with auxiliary systems such as signal recording/processing and analysis/decision/control systems via conductors 85 connected to control unit 25. Those skilled in the art can appreciate that signal transmission between sensors 75, 83 and control unit 25 to the auxiliary systems may be wireless. In that event, the electrode 60 would include a miniaturized transmitter mounted on an outer surface thereof.

The electrical sensors of the electrodes of the present invention are used to detect changes in brain activity, which sensors signal the control system 25 to initiate, and subsequently to terminate, the cooling therapy process, whether cooling or some other modality. It is to be understood that the signals from the sensors may arise from temperature, chemical or other biological phenomena that can be used to detect brain state changes. As the valves are automatically opened, the pressure difference, cause the refrigerant to flow into the shaft and cool the cooling elements 63; in the case of coolants, or a micropump 107, see FIG. 5a, is used to circulate the said coolant through the cooling elements 63. Once the safety limit is reached or the abnormal/undesirable activity has subsided, or the task of testing and mapping cortical functions has been completed, a micropump 107, see FIG. 5a, withdraws the refrigerant or coolant back into reservoir 43 to terminate the therapeutic intervention. Depending on the application, the electrode 60 or another electrode as disclosed herein, may be configured to sense and cool in one-, two- or three-dimensions by deploying into or retracting from the tissue, extendible elements in the x-, y-, and z-planes. Additionally, the shaft portion itself may comprise cooling surfaces to enhance and speed-up the cooling effect. In FIG. 4a, electrode 60, 93 or 150, as described herein, implanted into the brain is connected to control unit 25 placed under the skin, such as in the chest area, through conductors 23, 85, 97 or 177, or in some applications wirelessly via telemetry, and coolant or refrigerant flows through tubes 99 to reservoir 43 also placed in the chest area. The control units 25 generally comprise a processor or a microprocessor or a digital signal processor, memory for storing instructions, and a battery. The reservoir 43 may include tanks for coolant or pressurized cans for refrigerant. It is to be understood that the control units 25 and reservoir 43 may be placed at any convenient and accessible location on the body such as in or on the skull as disclosed in U.S. Pat. No. 6,560,486 of Ivan Osorio, or outside the body/skin. FIG. 4a depicts one of several possible locations of the control/storage units and FIG. 4b depicts a schematic representation of the operation of the device. Details of operation of the mechanical components are indicated in FIGS. 5a and 5b. For purposes of clarity, many of the Figures do not show the electrical conductors or sensors. The base of the electrode 11 includes micropumps 107 and microactuators 109 to pump and control the flow of the coolant or refrigerant into the shaft portion 113. The flow of the coolant or the refrigerant is controlled by valves 115. In an embodiment having extendable tubes, screws 117 are connected to the top of the extendable tubes via a plate 123, which can be used to push the extendible tubes into the target tissue, once the shaft portion is positioned within the tissue. The screws 117 can be operated manually by using motors connected to the control units 25. The flexible but less deformable or more rigid, compared to stiff tubes in other embodiments disclosed herein, inner tubes 125 are directed into the tissue by guides 127 attached to the shaft portion. Those having skill in the art can appreciate that mandrels can also be used to push the extendable tubes into the target tissue and then withdrawn, leaving the tubes outside the main shaft and in contact with the target tissue; the mandrels or extendible tubes or elements may be made of materials that are malleable or are "intelligent," such as memory metal alloy (e.g. biocompatible nickel-titanium shape memory metal alloy), which remembers its original pre-determined shape. The tubes containing coolant or refrigerant are sealed using medical, biocompatible seals 133 to prevent leakage of coolant or refrigerant into the surrounding tissue. Cooling through the extendable tubes can be accomplished by either a coolant or a refrigerant. In case of a coolant, the pump 107 circulates the coolant through the extendible tubes, which have a dividing wall for the return path of the coolant, similar to that shown in the inset in FIG. 3a. If a refrigerant is used to apply cooling therapy to the target tissue, an appropriate valve 115 is opened through the use of actuators 109 and the chilled refrigerant expands into the shaft portion of the electrode and the extendable tubes thereby cooling the tubes; a wall dividing the extendible tubes may not be required in this case. The extendible tubes in this case can be simply hollow as there is no free circulation of the refrigerant. To terminate cooling, the actuators are used to close the previously opened valve and open another valve to thereby enable a pump to withdraw the coolant or the refrigerant from the shaft portion. The pressure and temperature in the tubes are controlled by the control units 25.

For an application using refrigerant instead of coolant, any low pressure and nonflammable refrigerant may be used, such as those commonly used for pressurized air cleaners, i.e., tetrafluoroethane. The refrigerant is maintained at an elevated pressure in a storage unit 43, a microactuator 109 opens the valve 115 allowing the pressure differential of the refrigerant to cause the refrigerant to flow into the shaft portion or the extendible tubes as determined by the particular embodiment being used for the application to thereby rapidly cool the target tissue. Those familiar with the art appreciate that a valve may also open or close automatically due to the flow direction or pressure gradients, without actually needing an actuator to control it. In addition, the used refrigerant may be vented out into the air or it may be stored in a container adjacent to the reservoir 43. When cooling therapy needs to be terminated, a pump 107 withdraws the refrigerant from the tubes after a valve is opened that facilitates flow of the coolant in the appropriate direction. Existing miniature or micro-actuators using various technologies, including but not limited to piezoelectric, capacitive, electrochemical or magnetic actuators, may be used for this purpose. Similarly, existing pumps that are small enough to fit in the electrode structure and with appropriate flow rate in the range of approximately 1 microliter/sec to 1 milliliter/sec, may be used.

It is to be understood that for some applications, the extendable cooling elements hereinbefore described may be replaced with solid highly thermally conductive elements. In that event, the coolant or refrigerant resides in the shaft portion or at the base of the electrode and is spaced apart from the material exposed to the tissue, thereby obviating the need to use seals. Cooling is achieved by passive conduction through the solid, highly thermally conductive tubes. In this mode, the protruding elements are exposed to the coolant, refrigerant or other suitable media at the top of the electrode and cooling is passively transferred to the target tissue through the high thermal conductivity of the elements or the shaft portion. Materials of high thermal conductivity that can be used include, but are not limited to, carbon nanotubes, ceramics and other carbon or silicon composites. If a coolant is used, it can be recirculated indefinitely, provided its thermo-physical properties remain unchanged and it does not become contaminated. For refrigerants, replacement is obviously required before the contents of pressurized containers become depleted. The control units may have sensors to check the physical characteristics of the coolant and refrigerant supply such as pressure, temperature, etc., and may be programmed to alert the user as to the status of those characteristics.

Figure 6A:
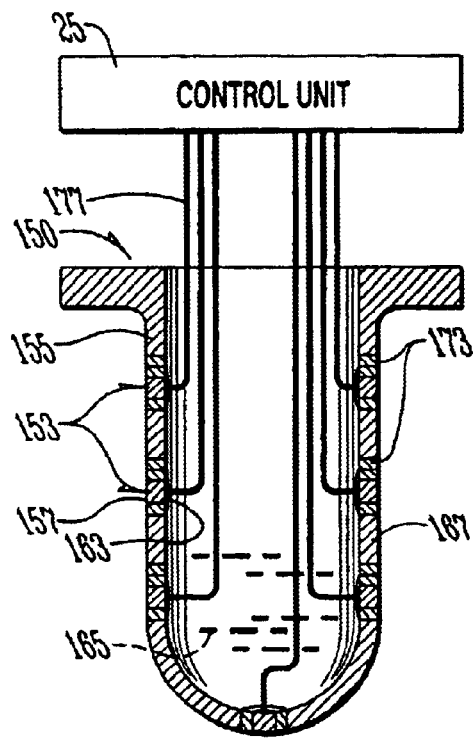
FIGS. 6a and 6b depict a modified embodiment of the multi-purpose electrode for detection and control of changes in brain state, using thermoelectric devices for applying cooling therapy, according to the present invention
Figure 6B:
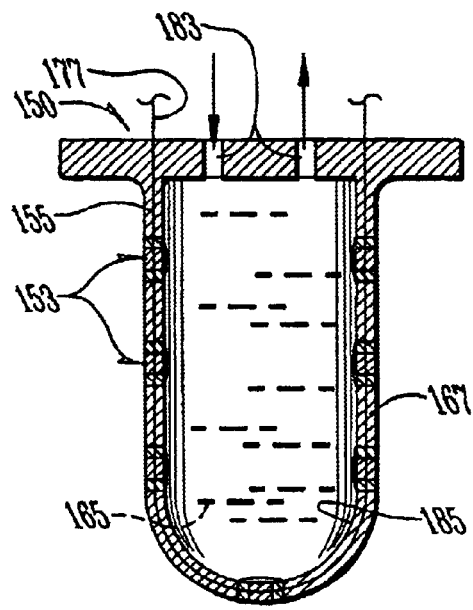

Another modified embodiment 150 of the electrode of the present invention is depicted in FIGS. 6a and 6b wherein cooling therapy is administered by using thermo-electric (TE) devices 153. In this embodiment 150, the TE devices 153 are placed in the shaft portion 155 whereat the cooled side surfaces 157 of the devices 153 are exposed to target tissue while the warmed surfaces 163 of the devices are inside the shaft portion, away from the tissue and facing the coolant or refrigerant 165 flowing therethrough. The TE devices 153 in the shaft portion 155 are separated from each other by insulation 167 as hereinbefore disclosed. Other electrical, thermal, chemical or physical sensors 173 can be placed in the shaft portion 155 of the electrode 150 for recording relevant signals as disclosed herein. Those skilled in the art can appreciate that the location of these sensors 173 in relation to the TE devices 153 or any other cooling elements, may vary depending on the application and the type of signals being monitored or recorded. The sensors 173 are connected to control units 25 via conductors 177; for some applications, communication between sensors 173 and control units 25 may be wireless if appropriate. Openings 183 provide access for coolant or refrigerant flowing into the shaft portion 155. As with other embodiments disclosed herein, seals are used to prevent the leakage of coolant or refrigerant into the surrounding target tissue. The shaft/electrode of the present invention as depicted in FIG. 6b does not require seals as there are no openings into the target tissue; thus, coolant or refrigerant can flow freely within inner wall 185 and thereby be in thermal contact with the warmed surfaces 163 of the TE devices 153. The extent of the insulation may be varied according to the application.

Those skilled in the art can appreciate that while cooling is the preferred method for control of state changes, safe increases in tissue temperature may be induced to control brain state changes, via the electrodes disclosed herein. By enhancing inherent noise through augmented Brownian motion of ions and vibrations of membrane proteins especially of those associated with ion channels or exocytotic sites, temperature elevations may "scramble" signal transmission between neurons or structures. Although the disclosure herein describes the use of coolants, those familiar with the art appreciate that tissue temperature can also be elevated within safe limits using liquids or other means to control brain tissue state changes.

It is to be understood that while certain forms of the present invention have been illustrated and described herein, it is not to be limited to the specific forms or arrangement of parts described and shown.

What is claimed and desired to be covered by Letters Patent is as follows:

1. A multi-purpose electrode mechanism for prediction or detection and control of changes in brain state, comprising;
   (a) a shaft portion structured for insertion into target tissue of the brain of a subject patient;

(b) cooling means configured to operatively apply cooling therapy to the target tissue;

(c) sensing means including at least one sensor monitoring a biological signal of the subject patient;

(d) control means responsive to the sensing means wherein the control means is structured to, in response to signals from the sensing means that indicate the occurrence of a change of state, automatically cause the cooling means to initiate or terminate the cooling therapy; and (e) an energy source for powering the various components of the multi-purpose electrode mechanism.

2. The multi-purpose electrode mechanism as described in claim 1, wherein the cooling means includes at least one extendable element housed within the shaft portion and structured to be extended outwardly from the shaft portion.

3. The multi-purpose electrode mechanism as described in claim 2, wherein the at least one extendable element is extended manually.

4. The multi-purpose electrode mechanism as described in claim 2, wherein the cooling means includes motor means structured to extend the at least one extendable element outwardly from the shaft portion into the target tissue.

5. The multi-purpose electrode mechanism as described in claim 2, wherein the at least one extendable element includes at least one cooling element constructed of a solid material having high thermal conductivity.

6. The multi-purpose electrode mechanism as described in claim 5, wherein the cooling means includes:

(a) a reservoir for containing coolant; and (b) pumping means structured to pump coolant to and from the reservoir and to the at least one cooling element.

7. The multi-purpose electrode mechanism as described in claim 5, wherein the cooling means includes:

(a) a refrigerant source containing refrigerant at an elevated pressure;

(b) distribution means for distributing the refrigerant from the refrigerant source to the at least one cooling element; and (c) means for removing the refrigerant from the cooling element or from the shaft portion.

8. The multi-purpose electrode mechanism as described in claim 2, wherein the at least one extendable element includes a hollow cooling element with a closed distal end.

9. The multi-purpose electrode mechanism as described in claim 8, wherein the at least one cooling element includes a dividing wall extending from near the proximal end to near the distal end of the at least one cooling element that separates the at least one cooling element into side-by-side first and second channels with fluid flow communication between the first and second channels at the distal end of the at least one cooling element.

10. The multi-purpose electrode mechanism as described in claim 9, further including:

(a) a reservoir for containing coolant; and (b) pumping means structured to pump coolant to and from the reservoir and through the at least one cooling element.

11. The multi-purpose electrode mechanism as described in claim 9, wherein the cooling means includes:

(a) a refrigerant source containing refrigerant at an elevated pressure;

(b) distribution means for distributing the refrigerant from the refrigerant source to the at least one cooling element; and (c) means for removing the refrigerant from the cooling element or from the shaft portion.

12. The multi-purpose electrode mechanism as described in claim 2, wherein:

(a) the at least one of the extendable element includes at least one sensing element; and (b) the sensing means includes at least one sensor positioned in the at least one extendible element.

13. The multi-purpose electrode mechanism as described in claim 1, wherein the sensing means includes at least one sensor mounted on the shaft portion to operatively contact target tissue adjacent thereto.

14. The multi-purpose electrode mechanism as described in claim 1, further comprising:

(a) stimulation means having at least one electrical contact structured to operatively apply electrical stimulation therapy to the target tissue; and (b) the control means, in response to signals from the sensing means that indicate the occurrence or presence of a change of state, is structured to automatically cause the stimulation means to initiate or terminate the electrical stimulation therapy.

15. The multi-purpose electrode mechanism as described in claim 1, wherein the cooling means includes at least one thermoelectric device, the thermoelectric device being cooled on the hot surface by a coolant or a refrigerant.

16. The multi-purpose electrode mechanism as described in claim 1, wherein the cooling means includes:

(a) a reservoir for containing coolant;

(b) an inner input tube with the shaft portion defining a cavity surrounding the inner input tube; and (c) pumping means structured to pump coolant from the reservoir from the reservoir, to and through the inner input tube into the cavity, and from the cavity back to the reservoir.

17. The multi-purpose electrode mechanism as described in claim 1, wherein the cooling means includes:

(a) a refrigerant source containing refrigerant at an elevated pressure;

(b) an inner input tube with the shaft portion defining a cavity surrounding the inner input tube; and (c) distribution means for distributing the refrigerant from the refrigerant source, to and through the inner input tube into the cavity, and from the cavity to venting means for venting refrigerant into a receiving means.

18. The multi-purpose electrode mechanism as described in claim 1, wherein the sensing means and control means are structured to sense in one-, two-, and/or three-dimensional configurations.

19. The multi-purpose electrode mechanism as described in claim 1, wherein the sensing means is structured to sense chemical signals arising from one of the group consisting of ions, neurotransmitters, proteins and pH.

20. The multi-purpose electrode mechanism as described in claim 1, wherein the sensing means is structured to sense physical signals arising from one of the group consisting of infrared, pressure, motion/vibration and acoustics.

21. The multi-purpose electrode mechanism as described in claim 1, wherein the sensing and control means include at least one electrical sensing device and at least one thermal and electrical device.

* * * * *